(12) United States Patent
Sain

(10) Patent No.: US 6,533,417 B1
(45) Date of Patent: Mar. 18, 2003

(54) METHOD AND APPARATUS FOR RELIEVING EYE STRAIN AND FATIGUE

(75) Inventor: Sun Sain, Morrison, TN (US)

(73) Assignee: Evian Corporation, Inc., Atlanta, GA (US)

( * ) Notice: Subject to any disclaimer, the term of this patent is extended or adjusted under 35 U.S.C. 154(b) by 75 days.

(21) Appl. No.: 09/798,131

(22) Filed: Mar. 2, 2001

(51) Int. Cl.[7] ................................................. A61B 3/00
(52) U.S. Cl. ...................................................... 351/203
(58) Field of Search ................................ 351/203, 237, 351/239, 243, 224, 226; 345/600

(56) References Cited

U.S. PATENT DOCUMENTS

| | | | |
|---|---|---|---|
| 3,861,790 A | * 1/1975 | Tamura | 351/237 |
| 5,051,931 A | 9/1991 | Cheu et al. | 364/550 |
| 5,515,069 A | 5/1996 | Dillon, III | 345/6 |
| 5,565,949 A | * 10/1996 | Kasha, Jr. | 351/224 |
| 5,825,460 A | * 10/1998 | Kohayakawa | 351/237 |
| 5,933,130 A | 8/1999 | Wagner | 345/145 |
| 6,042,231 A | 3/2000 | Fatch | 351/203 |
| 6,091,399 A | * 7/2000 | Sumiyoshi et al. | 345/600 |
| 6,139,149 A | 10/2000 | Shafer et al. | 351/203 |

* cited by examiner

Primary Examiner—George Manuel
(74) Attorney, Agent, or Firm—Birch, Stewart, Kolasch & Birch, LLP

(57) ABSTRACT

A method and apparatus for providing eye exercises that can help relieve eye strain and eye fatigue. The eye exercises can be accessed by running a computer program on the user's computer or accessing a website. The eye exercises involve displaying a single focus object on a computer screen and moving the focus object according to predetermined patterns and/or changing the size of the focus object on the computer screen. By viewing the focus object and following it on the computer screen, the user can exercise his or her eyes and thereby relieve eye fatigue and eye stress.

29 Claims, 7 Drawing Sheets

METHOD AND APPARATUS FOR RELIEVING EYE STRAIN AND FATIGUE

BACKGROUND OF THE INVENTION

1. Field of the Invention

The present invention relates to eye exercise devices and more particularly, to a method and apparatus for relieving eye strain and fatigue by providing computer-implemented eye exercise programs.

2. Discussion of the Related Art

A growing number of individuals are engaging in computer-based activities such as surfing the Internet, conducting online transactions, communicating via e-mails, etc. Such activities often involve viewing the computer screen and focusing on small objects for an extended time period. Due to the computer-based activities, many people suffer from eye fatigue and discomfort daily. Eye strain and eye fatigue can cause a deterioration of eyesight, vision failures and the development of cornea and other eye diseases, and contribute to the increase in use of glasses, contact lenses and vision-corrective eye surgeries.

Various eye exercise devices for relieving eye strain and fatigue are known. For instance, U.S. Pat. No. 5,515,069 to Dillion, III teaches a plurality of light sources installed around a video display terminal. The light sources are lit in a predetermined pattern to provide a three-dimensional eye-stimulating image. By viewing the image, the viewer's eyes are exercised to relieve eye strain and fatigue.

U.S. Pat. No. 6,042,231 to Fatch and U.S. Pat. No. 5,051,931 to Cheu et al. teach computer programs that generate images on a computer screen for exercising the eyes. The Fatch program displays two associated images along a horizontal line on the viewer's computer screen. The viewer is requested to focus on the images so that the viewer sees a single merged image. Then the two images slowly move away from each other along the horizontal line. If the viewer can no longer see the single merged image, the viewer is requested to press a key on the keyboard, which stops the program. The viewer is given a score for this exercise and the exercise is repeated. By viewing the two associated images as they move apart, the viewer's eyes are exercised.

Similar to the Fatch program, the Cheu et al. program displays two associated objects that move slowly away from each other. However, the associated objects displayed by the Cheu et al. program have different colors (e.g., red and green) and the viewer is required to wear a specially designed goggle having color lenses to partake in this exercise. The Cheu et al. program also offers eye movement exercises. Two to four letters of the alphabet appear randomly on the computer screen for a predetermined time period, e.g., 3 seconds. Then the letters disappear and the viewer is requested to enter via a keyboard the letters that the viewer has seen within a certain time limit, e.g., 2 seconds. The viewer is given a score for participating in these exercises. By viewing the associated images and the letters on the screen, the viewer's eyes are exercised.

In all these conventional eye exercise devices, however, there are problems and drawbacks. In the Dillion, III system, the installation of the plurality of light sources and support bars around the viewer's computer screen requires a significant amount of installation space and is a cumbersome task. Further, the appearance of the system is unattractive and may not be desirable for public places such as offices. In both the Fatch and Cheu et al. computer programs, the viewer is required to enter a viewer response during the exercise, based upon which a score is generated. This may be an effective way to keep the interests of the viewer. Unfortunately, it also means the viewer must stay alert during the entire exercise so that the viewer can quickly enter the viewer's responses. However, having to stay alert for a certain time duration and having to enter responses quickly can create a stressful environment for the viewer and may deter the use of the programs especially when the viewer is already tired. Furthermore, if the viewer is already tired before he or she begins the exercise, then the viewer is likely to enter inaccurate responses, which will result in scores that do not accurately reflect the viewer's eye condition.

Accordingly, there is a need for an improved method and apparatus for relieving eye strain and eye fatigue which can be used in a more relaxed environment without requiring the input of a viewer's responses during the exercise, and which can be easily used and installed without affecting the overall scheme and appearance of the viewer's computer system.

SUMMARY OF THE INVENTION

The present invention is directed to a method and apparatus for providing computer-implemented eye exercises for relieving eye strain and eye fatigue. The eye exercises are provided by running a computer program on a user's computer, or accessing a designated website through the Internet. In the eye exercises, a single focus object appears on the user's computer screen. The focus object moves on the computer screen according to predetermined patterns and/or changes its size on the computer screen. By viewing the focus object and following it on the computer screen, the user can exercise his or her eyes and the eye fatigue and eye stress can be reduced significantly. No interaction or user response is needed during the exercises.

Therefore, the present invention provides simple yet effective eye exercise programs which can be used in a more relaxed environment without requiring the input of a user's response during the exercise, and which can be easily used and installed without affecting the overall scheme or appearance of the user's computer system.

DETAILED DESCRIPTION OF THE PREFERRED EMBODIMENTS

Figure 1:
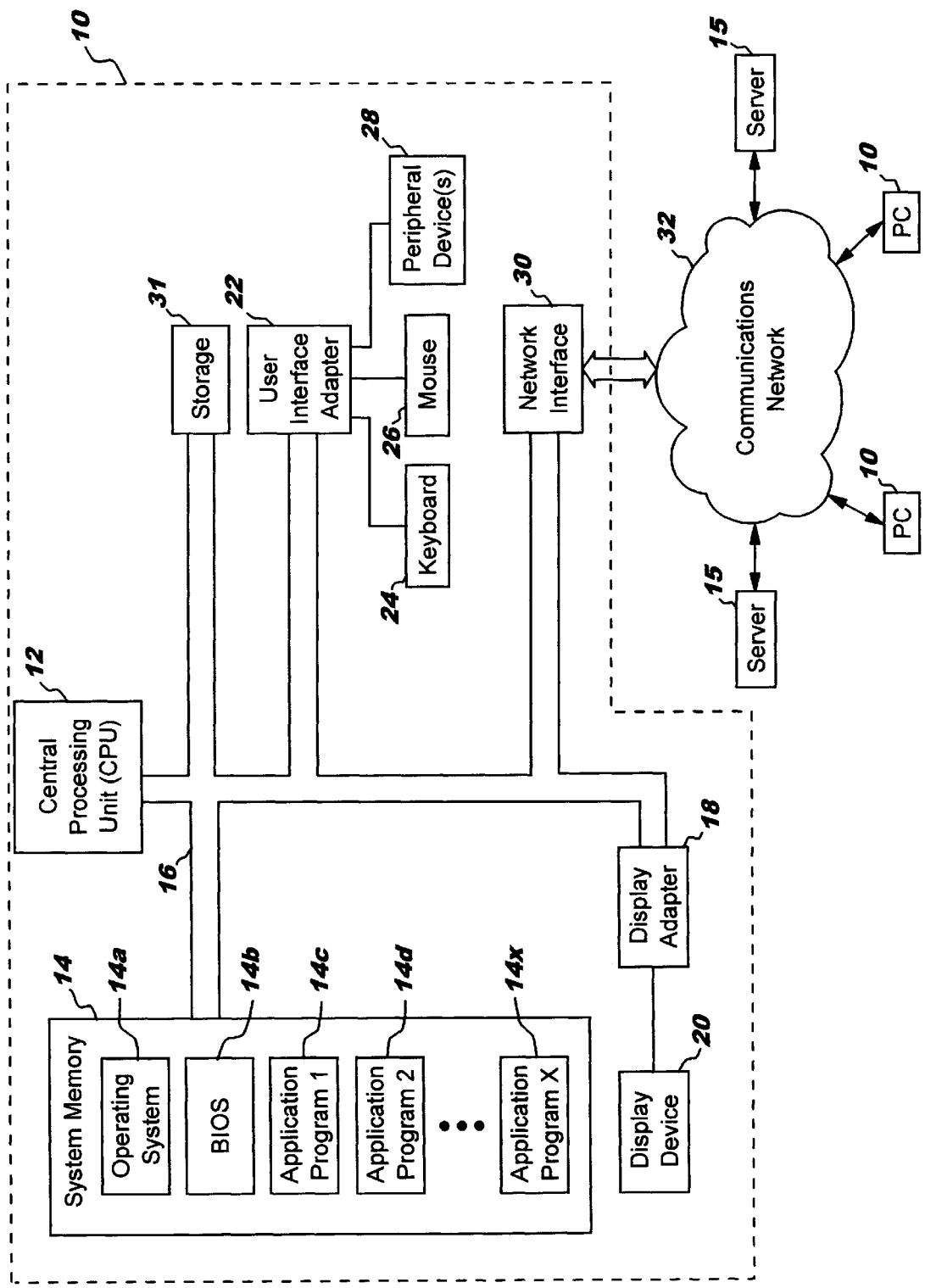
FIG. 1 is a block diagram of a conventional personal computer in which a preferred embodiment of the present invention may be practiced.

FIG. 1 is a block diagram of a typical personal computer (PC) 10 in which a preferred embodiment of the present invention may be practiced. As shown in FIG. 1, the PC 10 includes a central processing unit (CPU) 12, a system memory 14 including Read Only Memory (ROM) and Random Access Memory (RAM), and a system bus 16 for enabling communication between the CPU 12 and the components of the PC 10 in accordance with known techniques. The PC 10 also includes a display adaptor 18 connected to a display device 20 such as a monitor or an LCD screen, a user interface adaptor 22 connected to a keyboard 24, a mouse 26 and/or any other peripheral device (s) 28 such as a stylus, and a network interface 30 for communicating with other PCs 10 and servers 15 through a communications network 32 such as the Internet, an intranet, an extranet, etc. The PC 10 can further include storage 34 which may be a hard drive, a floppy disk drive, a CD-ROM drive, etc. The PC 10 may be a desktop, laptop, hand held, work station, server, or any other computer device, and may operate in a client-server or distributed network environment.

The system memory 14 typically stores operating system 14a, Basic Input/Output System (BIOS) 14b, and a plurality of application programs 14c, 14d, ... 14x. The operating system 14a provides the basic interface between the CPU 12, the user and the application programs 14b–14x. The operating system 14a processes instructions issued by the user and executes them according to known techniques. The BIOS 14b is a set of basic routines that are used to transfer information between the components of the PC 10. The application programs 14b–14x are computer programs implementing specific application functions and features. All of these configurations, as well as the appropriate communications hardware and software, are well known in the art.

A preferred embodiment of the present invention is now described. The preferred embodiment of the present invention is directed to a computer program, method and apparatus for providing eye exercises that can help relieve eye strain and eye fatigue. The computer program can be installed in the system memory 14 or the storage 34, or can be downloaded or provided directly from a server or website through the communications network 32. The computer program configures the user's computer to display a series of screen images on the display device for viewing by the user. According to the present invention, the user's eyes are exercised and relieved from fatigue and muscle strain by viewing these screen images. No interaction or user response is needed during the eye exercises of the present invention.

More specifically, the eye exercises of the present invention include six different eye exercises. In each of the eye exercises, a single focus object appears on a user's display device such as a computer screen. Then the focus object moves on the computer screen according to predetermined patterns and/or the size of the focus object changes. The focus object may be in particular color, e.g., white, and can be in the shape of a circle, a rectangle, triangle, or other shape. Depending on the application, any shape and/or color can be used. If the focus object is in particular color, e.g., white, the computer screen may display a background color such as green so that the user can recognize the focus object without straining the user's eyes. In some embodiments, the system can be configured such that a particular image that interests the user, such as a cartoon image if the user is a child, a picture of the user's family, or other image, is displayed inside the focus object. For instance, if the focus object is a circle, a picture of a cartoon character may appear inside the circle, so as to maintain the interest of the user as the user participates in the eye exercises. The system is configured so that the user can design his or her own eye exercise program by selecting one or more of the six eye exercises and the order in which these exercises start. The user can also dictate the number of times that each exercise is repeated before a next exercise begins.

Figure 2:
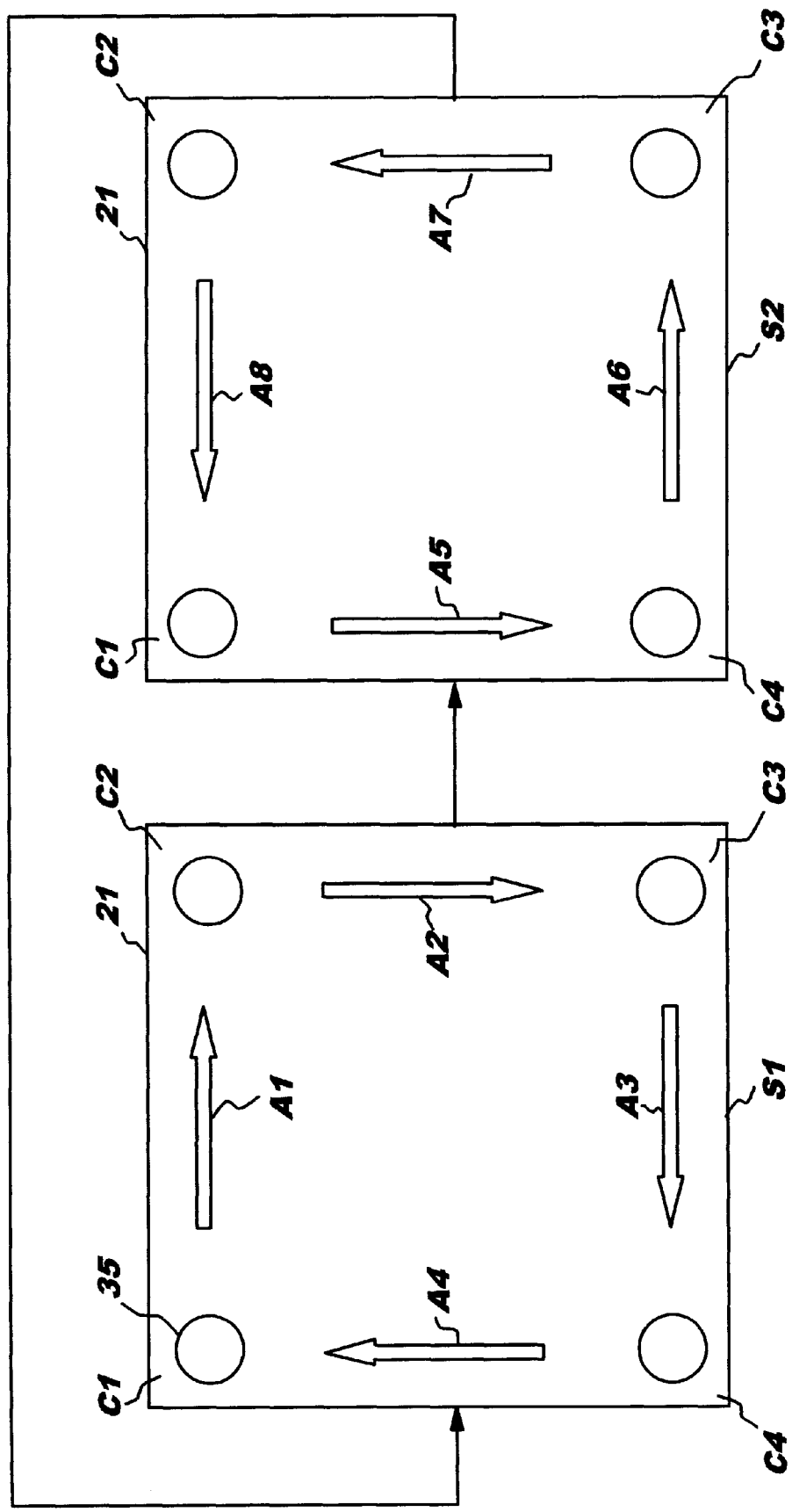
FIG. 2 is an example of a first eye exercise implemented by a computer according to the present invention.

FIG. 2 shows an example of a first eye exercise implemented by a computer according to the present invention. In this example, the focus object is a circle, but any other shape can be used. As shown in FIG. 2, at the beginning of the first eye exercise, in a first step S1, a single focus object 35 appears at a first corner C1 (top left) of a user's computer screen 21 or other display device. The focus object 35 then moves in a clockwise direction. Particularly, the focus object 35 moves horizontally across the computer screen 21 to a second corner C2 (top right) of the computer screen 21 as indicated by an arrow A1. Then the focus object 35 moves down vertically to a third corner C3 (bottom right) of the screen 21 as indicated by an arrow A2. Then the focus object 35 moves horizontally across the screen 21 to a fourth corner C4 (bottom left) of the screen 21 as indicated by an arrow A3. Then the focus object 35 moves up vertically to the first corner C1 as indicated by an arrow A4.

Then a second step S2 is performed wherein the focus object 35 moves in a counterclockwise direction. Particularly, the focus object 35 in the first corner moves down vertically to the fourth corner C4 of the screen 21 as indicated by an arrow A5. Then the focus object 35 moves horizontally across the screen 21 to the third corner C3 of the screen 21 as indicated by an arrow A6. Then the focus object 35 moves up vertically to the second corner C2 of the screen 21 as indicated by an arrow A7. Then the focus object 35 moves horizontally across the screen 21 to the first corner C1 as indicated by an arrow A8.

Then the process returns to the first step S1 and the first and second steps S1 and S2 are repeated any number of times according to the user's selection or based on a pre-programmed number. To exercise the user's eyes to relieve eye stress and eye fatigue, the user focuses on the object 35 and follows the object 35 on the screen 21.

In one embodiment, when the focus object 35 arrives at a new corner from a previous corner, a hole (e.g., an image of a golf hole) appears on the screen 21 and the focus object 35 drops into the hole, disappearing from the screen 21. Then a new focus object 35 appears at the new corner and moves to another corner. This process is repeated each time the object 35 arrives at a new corner. By providing a golf hole image or the like, the interest of the user may be maintained while the user participates in the exercise. Other schemes may be used to maintain the interest of the user during the eye exercises.

Figure 3:
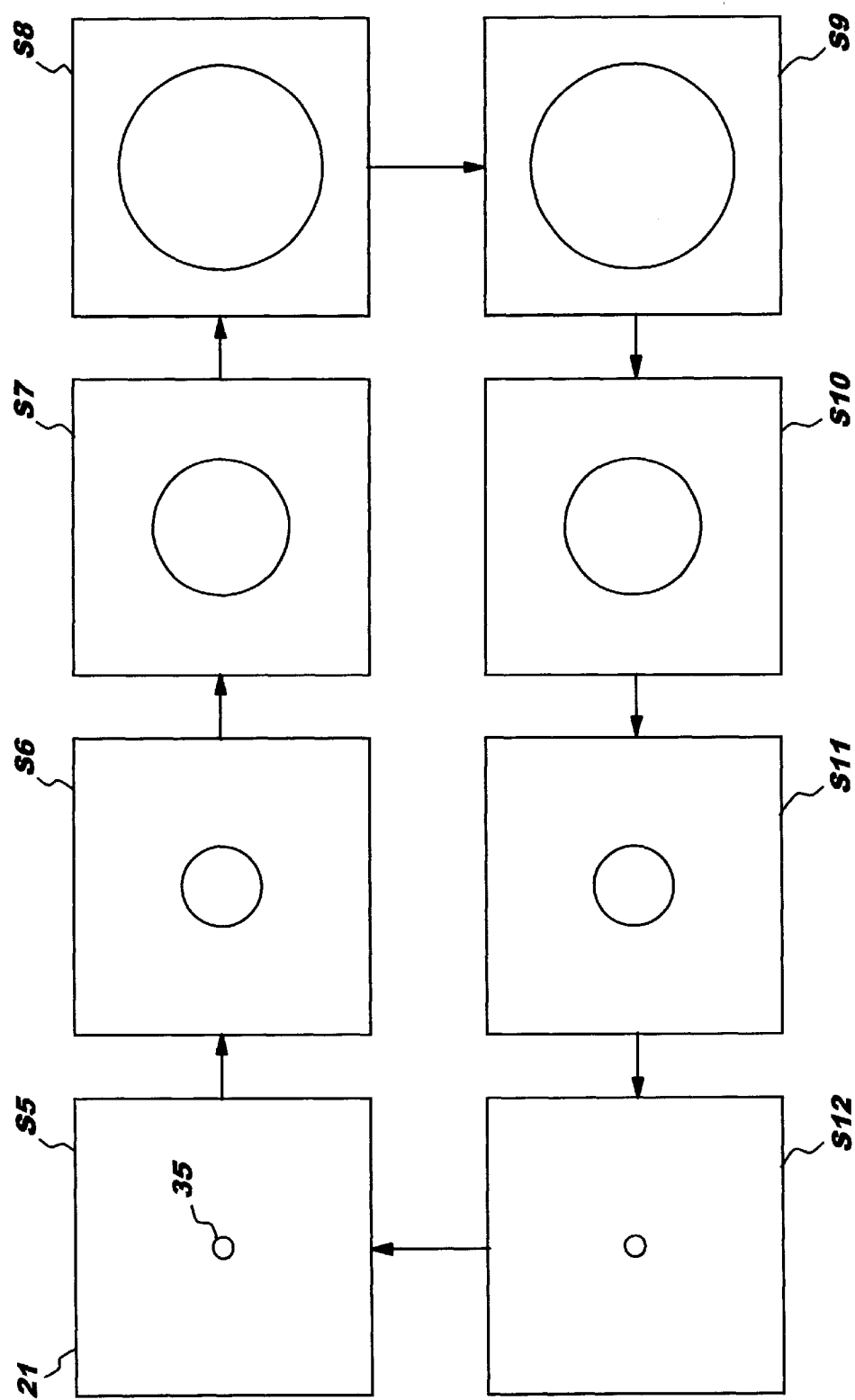
FIG. 3 is an example of a second eye exercise implemented by a computer according to the present invention.

FIG. 3 shows an example of a second eye exercise implemented by a computer according to the present invention. The second eye exercise displays a single focus object on the user's computer screen and gradually increases and decreases the size of the focus object. As shown in FIG. 3, in a first step S5 of the second eye exercise, the focus object 35 appears in the middle of the user's computer screen 21 as a small object. Then the size of the focus object 35 increases gradually in the subsequent steps S6–S8 (without changing the position of the object 35) until the focus object 35 fills substantially the entire screen 21. Then the size of the enlarged object 35 gradually decreases back to its initial size in the subsequent steps S9–S12. Then these steps S5–S12 are repeated for any number of times according to the user's selection or based on a pre-programmed number. To exercise the user's eyes, the user views the object 35 and focuses on it as the size of the focus object 35 changes.

Figure 4:
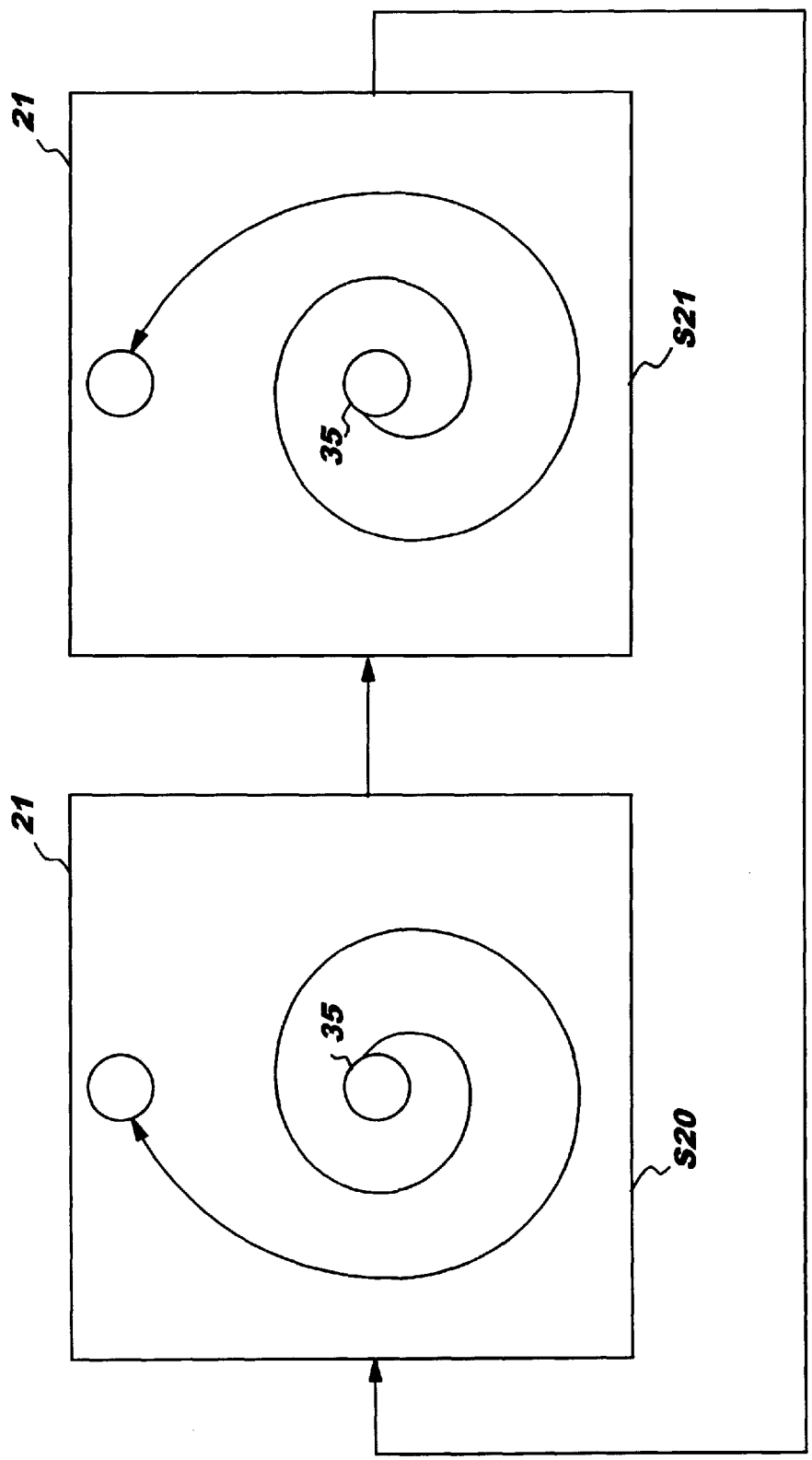
FIG. 4 is an example of a third eye exercise implemented by a computer according to the present invention.

FIG. 4 shows an example of a third eye exercise implemented by a computer according to the present invention. The third eye exercise involves displaying a single focus object on the user's computer screen and moving the object on the screen in spiral patterns. More specifically, as shown in FIG. 4, in a first step S20 of the third eye exercise, a focus object 35 appears at the center of the user's computer screen 21. Then the focus object 35 moves in a spiral pattern in a clockwise direction until it reaches a predetermined end position, e.g., a top middle portion of the screen 21. Once the focus object 35 reaches the predetermined end position, it disappears from the screen 21. Then a second step S21 is performed wherein another focus object 35 appears at the center of the screen 21. Then the focus object 35 moves in a spiral pattern in a counterclockwise direction until it reaches a predetermined end position. Once the focus object 35 reaches the end position, it disappears from the screen 21 and the exercise returns to the first step S20. In this manner, the steps S20 and S21 are repeated for any number of times according to the user's selection or based on a pre-programmed number. To exercise the eyes to relieve eye fatigue and eye strain, the user focuses on the object 35 while the object 35 moves on the screen 21 in spiral patterns.

Figure 5:
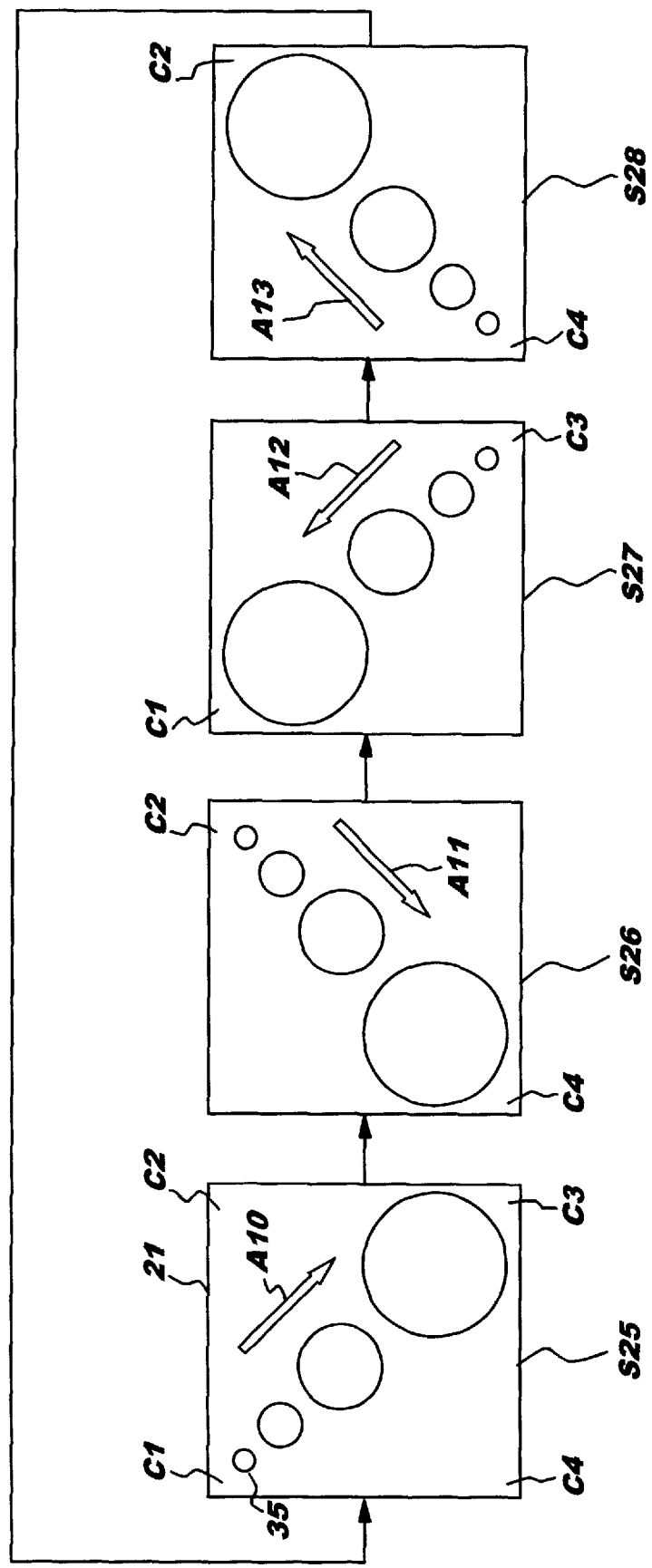
FIG. 5 is an example of a fourth eye exercise implemented by a computer according to the present invention.

FIG. 5 shows an example of a fourth eye exercise implemented by a computer according to the present invention. The fourth eye exercise displays a single focus object on the user's computer screen and moves it in diagonal directions while increasing the size of the focus object. More specifically, as shown in FIG. 5, at the beginning of the fourth eye exercise, a small focus object 35 appears at the first corner C1 of the user's computer screen 21 in a first step S25. Then the focus object 35 moves in a diagonal direction to the third corner C3 as indicated by an arrow A10 while the size of the focus object 35 increases. When the focus object 35 reaches the third corner C3, the first step S25 is completed and the object 35 disappears from the screen 21. Then a second step S26 is performed wherein another small focus object 35 appears at the second corner C2 of the screen 21. Then the focus object 35 moves in a diagonal direction to the fourth corner C4 as indicated by an arrow A11 while the size of the focus object 35 increases. When the focus object 35 reaches the fourth corner C4, the second step S26 is completed and the focus object 35 disappears from the screen 21. Then a third step S27 is performed wherein another small focus object 35 appears at the third corner C3 of the screen 21. Then the focus object 35 moves in a diagonal direction to the first corner C1 as indicated by an arrow A12 while the size of the focus object 35 increases. When the focus object 35 reaches the first corner C1, the third step S27 is completed and the object 35 disappears from the screen 21. Then a fourth step S28 is performed wherein another small focus object 35 appears at the fourth corner C4 of the screen 21. Then the focus object 35 moves in a diagonal direction to the second corner C2 as indicated by an arrow A13 while the size of the focus object 35 increases. When the focus object 35 reaches the second corner C2, the fourth step S28 is completed and the object 35 disappears from the screen 21. Then the fourth eye exercise returns to the first step S25. In this manner, the steps S25 to S28 are repeated for any number of times according to the user's selection or based on a pre-programmed number. To exercise the eyes, the user focuses on the object 35 and follows the object 35 on the screen 21 while the object 35 moves diagonally with increasing size.

In the fourth eye exercise, the starting position of the focus object 35 in the steps S25–S28 moves in a clockwise direction, i.e., from the corner C1 to C2 to C3 to C4 and so on. However, other variations are possible. For example, the starting position of the focus object in the steps S25–S28 may move in a counterclockwise direction, i.e., from the corner C1 to C4 to C3 to C2 and so on. In other embodiments, such modified steps may occur after the original steps S25–S28 are performed such that the starting position of the focus object moves in the clockwise direction and then in the counterclockwise direction.

Figure 6:
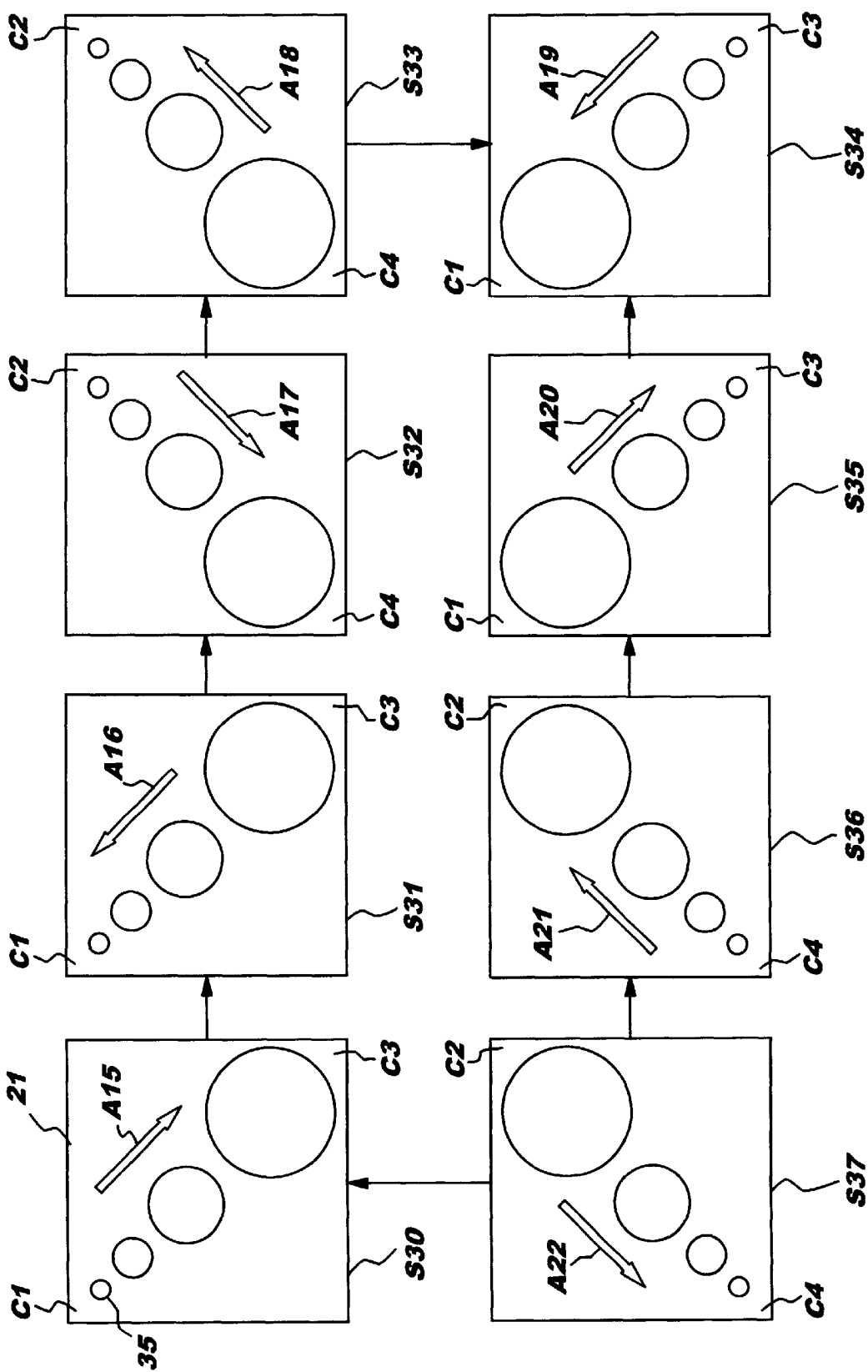
FIG. 6 is an example of a fifth eye exercise implemented by a computer according to the present invention.

FIG. 6 shows an example of a fifth eye exercise implemented by a computer according to the present invention. The fifth eye exercise is similar to the fourth eye exercise, but involves increasing and decreasing the size of the focus object as the object moves in diagonal directions. More specifically, as shown in FIG. 6, at the beginning of the fifth exercise, a small focus object 35 appears at the first corner C1 of the user's computer screen 21 in a first step S30. Then the focus object 35 moves in a diagonal direction to the third corner C3 as indicated by an arrow A15 while the size of the focus object 35 increases. When the focus object 35 reaches the third corner C3, the enlarged focus object 35 moves at a second step S31 in a reverse diagonal direction to the first corner C1 as indicated by an arrow A16 while the size of the enlarged focus object 35 decreases back to its initial size. When the focus object 35 reaches the first corner C1, the second step S31 is completed and the object 35 disappears from the screen 21.

Then a third step S32 is performed wherein a small focus object 35 appears at the second corner C2 of the screen 21. The focus object 35 moves in a diagonal direction to the fourth corner C4 as indicated by an arrow A17 while the size of the focus object 35 increases. When the focus object 35 reaches the fourth corner C4, the enlarged focus object 35 moves at a fourth step S33 in a reverse diagonal direction to the second corner C2 as indicated by an arrow A18 while the size of the enlarged focus object 35 decreases back to its initial size. When the focus object 35 reaches the second corner C2, the fourth step S33 is completed and the object 35 disappears from the screen 21.

Then a fifth step S34 is performed wherein a small focus object 35 appears at the third corner C3 of the screen 21. The focus object 35 moves in a diagonal direction to the first corner C1 as indicated by an arrow A19 while the size of the focus object 35 increases. When the focus object 35 reaches the first corner C1, the enlarged focus object 35 moves at a sixth step S35 in a reverse diagonal direction to the third corner C3 as indicated by an arrow A20 while the size of the enlarged focus object 35 decreases back to its initial size. When the focus object 35 reaches the third corner C3, the sixth step S35 is completed and the object 35 disappears from the screen 21.

Then a seventh step S36 is performed wherein a small focus object 35 appears at the fourth corner C4 of the screen 21. The focus object 35 moves in a diagonal direction to the second corner C2 as indicated by an arrow A21 while the size of the focus object 35 increases. When the focus object 35 reaches the second corner C2, the enlarged focus object 35 moves at an eighth step S37 in a reverse diagonal direction to the fourth corner C4 as indicated by an arrow A22 while the size of the enlarged focus object 35 decreases back to its initial size. When the focus object 35 reaches the fourth corner C4, the eighth step S37 is completed and the object 35 disappears from the screen 21.

Then the fifth eye exercise returns to the first step S30. In this manner, the steps S30 to S37 are repeated for any number of times according to the user's selection or based on a pre-programmed number. To exercise the eyes, the user views the object 35 on the screen 21 as the object 35 moves diagonally.

In the present example, the starting position of the focus object in the steps S30, S32, S34 and S36 moves in a clockwise direction, i.e., from the corner C1 to C2 to C3 to C4 and so on. However, other variations are possible. For example, the starting position of the focus object in these steps may move in a counterclockwise direction, i.e., from the corner C1 to C4 to C3 to C2 and so on. In other embodiments, such modified steps may occur after the original steps S30–S37 are performed such that the starting position of the focus object moves in the clockwise direction and then the counterclockwise direction.

Figure 7:
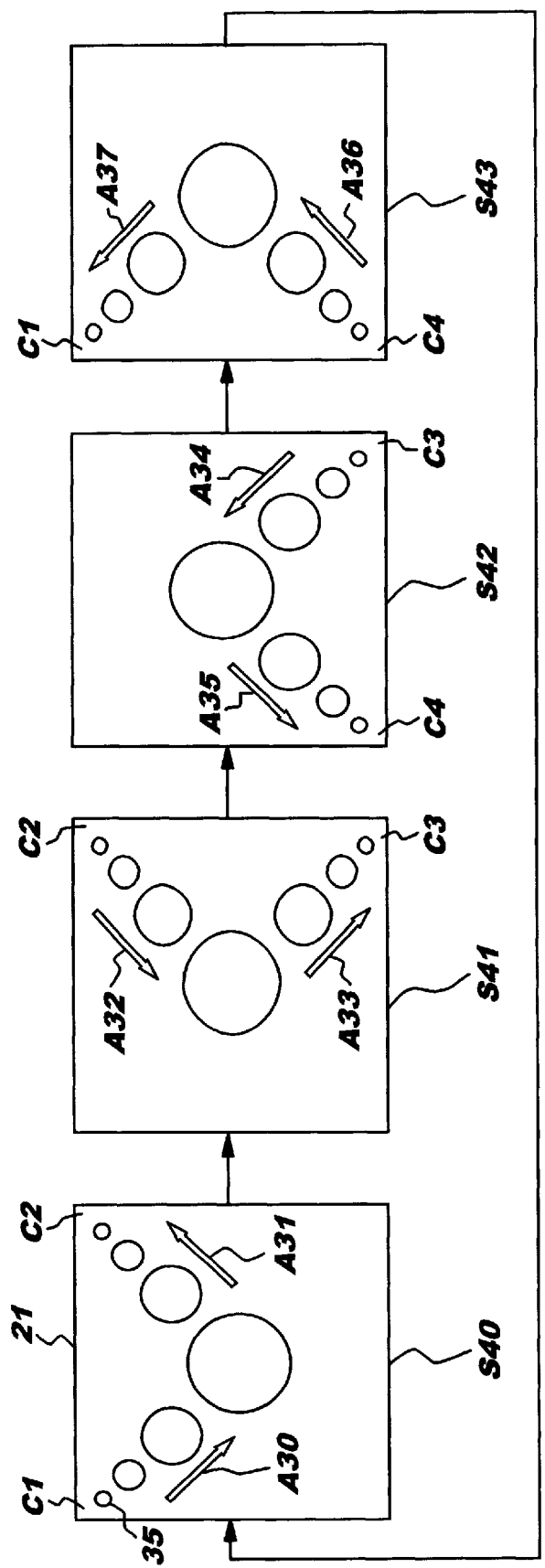
FIG. 7 is an example of a sixth eye exercise implemented by a computer according to the present invention.

FIG. 7 shows an example of a sixth eye exercise implemented by a computer according the present invention. The sixth eye exercise is similar to the fifth eye exercise, but involves moving the single focus object in an angle pattern while increasing and decreasing the size of the focus object. More specifically, as shown in FIG. 7, at the beginning of the sixth exercise, in a first step S40, a small focus object 35 appears at the first corner C1 of the user's computer screen 21. Then the focus object 35 moves in a diagonal direction to the center of the screen 21 as indicated by an arrow A30 while the size of the focus object 35 increases. Once the focus object 35 reaches the center of the screen 21, the enlarged focus object 35 moves in another diagonal direction (i.e., in an angle pattern) to the second corner C2 as indicated by an arrow A31 while the size of the enlarged focus object 35 decreases back to its initial size. When the focus object 35 reaches the second corner C2, the first step S40 is completed and the object 35 disappears from the screen 21.

Then a second step S41 is performed wherein a small focus object 35 appears at the second corner C2 of the screen 21. The focus object 35 moves in a diagonal direction to the center of the screen 21 as indicated by an arrow A32 while the size of the focus object 35 increases. Once the focus object 35 reaches the center of the screen 21, the enlarged focus object 35 moves in another diagonal direction to the third corner C3 as indicated by an arrow A33 while the size of the enlarged focus object 35 decreases back to its initial size. When the focus object 35 reaches the third corner C3, the second step S41 is completed and the object 35 disappears from the screen 21.

Then a third step S42 is performed wherein a small focus object 35 appears at the third corner C3 of the screen 21. The focus object 35 moves in a diagonal direction to the center of the screen 21 as indicated by an arrow A34 while the size of the focus object 35 increases. Once the focus object 35 reaches the center of the screen 21, the enlarged focus object 35 moves in another diagonal direction to the fourth corner C4 as indicated by an arrow A35 while the size of the enlarged focus object 35 decreases back to its initial size. When the focus object 35 reaches the fourth corner C4, the third step S42 is completed and the object 35 disappears from the screen 21.

Then a fourth step S43 is performed wherein a small focus object 35 appears at the fourth corner C4 of the screen 21. The focus object 35 moves in a diagonal direction to the center of the screen 21 as indicated by an arrow A36 while the size of the focus object 35 increases. Once the focus object 35 reaches the center of the screen 21, the enlarged focus object 35 moves in another diagonal direction to the first corner C1 as indicated by an arrow A37 while the size of the enlarged focus object 35 decreases back to its initial size. When the focus object 35 reaches the first corner C1, the fourth step S43 is completed and the object 35 disappears from the screen 21.

Then the sixth eye exercise returns to the first step S40. In this manner, the steps S40 to S43 are repeated for any number of times according to the user's selection or based on a pre-programmed number. To exercise the eyes, the user focuses on the object 35 and follows it on the screen 21 as the object 35 moves diagonally.

In this example, the starting position of the focus object in the steps S40 to S43 moves in a clockwise direction, i.e., from the corner C1 to C2 to C3 to C4 and so on. However, other variations are possible. For example, the starting position of the focus object in these steps may move in a counterclockwise direction, i.e., from the corner C1 to C4 to C3 to C2 and so on. In other embodiments, such modified steps may occur after the original steps S40–S43 are performed such that the starting position of the focus object moves in the clockwise direction and then the counterclockwise direction.

In some embodiments, the shape of the focus object in these eye exercises may change when the focus object disappears from the computer screen and a new focus object appears on the screen. This scheme helps to maintain the interest of the users. For instance, in the third eye exercise shown in FIG. 4, the focus objects shown in the steps S20 and S21 may differ in shape, color or configuration. If the focus object 35 in the step S20 was a circle, the focus object 35 in the shape of a star may appear in the step S21.

In accordance with the preferred embodiment, a menu page is provided on the user's computer screen prior to starting any of the eye exercises. The menu page enables the user to select appropriate parameters to design a user-specific eye exercise program. For instance, a menu page may identify a list of different parameters which the user can select to design the user-specific eye exercise program. Using the menu page, the user is able to design his or her own eye exercise program by making selections such as a selection of one or more of the first to sixth eye exercises discussed above, a selection of an order in which the eye exercises are executed, a selection of a particular shape and/or color of a focus object, a selection of a speed at which the focus object on the computer screen, a selection of a background color, a selection of a particular graphical image or picture to be displayed inside the focus object, a selection of a background music or song to be played while the eye exercises are carried out, and a selection of the number of times each exercise is repeated. Depending on the application, other selections are possible.

In one embodiment, predetermined images, which the user can select to add inside the focus object, are provided by the computer program or a designated website. In another embodiment, the user can insert inside the focus object an image from another source, such as a video clip, a photograph file, so that the user's personal photographs or pictures can be displayed inside the focus object. In still another embodiment, in FIG. 3, as the size of the focus object increases and decreases, the image inside the focus object may increase and decrease with the focus object, or remain at a fixed size.

In another embodiment, any combination of the first through sixth exercises can be pre-recorded on a recording medium such as a video tape, CD, DVD, etc., so that the user is able to exercise his or her eyes by playing the recording medium on a display device such as a television monitor and viewing the focus object on the monitor.

The present invention also encompasses the methods of doing business by establishing a website that provides the eye exercises of the present invention. For instance, a particular website may be created for providing these eye exercises online. A user may access this website, e.g., using a password, and can participate in a user-specific eye exercise program daily. The website may maintain a record of how many times each user has participated in their eye exercise program, how long the exercise program lasted, and the content of the exercise program. These records can be provided to the user or used by the website provider to provide other health related information to the user.

Accordingly, the present invention provides novel eye exercising method and apparatus, which are easy to use and effective in relieving eye stress and eye fatigue.

Although the present invention has been described with respect to a specific embodiment thereof, various changes and modifications may be suggested to one skilled in the art and it is intended that the present invention encompass such changes and modifications as they fall within the scope of the appended claims.

What is claimed is:

1. A method for relieving eye strain of a user, the method comprising the steps of:
   displaying a single focus object on a display screen;
   providing a plurality of eye exercises using the focus object, each of the eye exercises involving at least one of the following: moving the focus object in a predetermined pattern on the display screen, and changing a size of the focus object on the display screen, wherein the user's eyes are exercised by viewing the focus object on the display screen; and
   displaying a menu screen for receiving selections from the user, wherein the user's selections include at least one of the following: a selection of an order in which the eye exercises are executed, a selection of a particular shape and/or color of the focus object, a selection of a speed at which the focus object moves on the display screen, a selection of a background color, a selection of a particular graphical image or picture to be displayed inside the focus object, a selection of a background music or song to be played while the eye exercises are carried out, and a selection of the number of times each exercise is repeated.

2. The method of claim 1, wherein the plurality of eye exercises include a first eye exercise comprising the steps of:
   moving the focus object from a first corner of the display screen to a second corner of the display screen,
   moving the focus object from the second corner to a third corner of the display screen,
   moving the focus object from the third corner to a fourth corner of the display screen, and
   moving the focus object from the fourth corner to the first corner.

3. The method of claim 2, wherein, in the first eye exercise, the size of the focus object is maintained while the focus object moves from one corner to another corner on the display screen.

4. The method of claim 2, wherein, in the first eye exercise, a shape of the focus object is changed when the focus object begins to move from one corner to another on the display screen.

5. The method of claim 1, wherein the plurality of eye exercises include a third eye exercise comprising the steps of:
   providing the focus object at a center of the display screen, and
   moving the focus object in a spiral pattern.

6. The method of claim 1, wherein, in the providing step, the focus object is moved in the predetermined pattern as a shape of the focus object changes on the display screen.

7. The method of claim 1, wherein the focus object is a circle, a triangle, or a rectangle.

8. A method for relieving eye strain of a user, the method comprising the steps of:
   displaying a single focus object on a display screen;
   providing a plurality of eye exercises using the focus object, each of the eye exercises involving at least one of the following: moving the focus object in a predetermined pattern on the display screen, and changing a size of the focus object on the display screen, wherein the user's eyes are exercised by viewing the focus object on the display screen, and wherein the focus object is a circle, a triangle, or a rectangle; and
   displaying an image inside the focus object.

9. The method of claim 1, wherein said displaying and providing steps are implemented on a computer by a computer program.

10. The method of claim 1, wherein said displaying and providing steps are implemented by playing information recorded on a recording medium.

11. The method of claim 1, wherein the user need not input a response while viewing the focus object in the eye exercises.

12. A method for relieving eye strain of a user, the method comprising the steps of:
    displaying a single focus object on a display screen; and
    providing a plurality of eye exercises using the focus object, each of the eye exercises involving at least one of the following: moving the focus object in a predetermined pattern on the display screen, and changing a size of the focus object on the display screen,
    wherein the user's eyes are exercised by viewing the focus object on the display screen, and
    wherein the plurality of eye exercises include a second eye exercise comprising the steps of:
    providing the focus object of an initial size at a center of the display screen,
    increasing the size of the focus object until the focus object reaches a predetermined enlarged size, and
    then decreasing the enlarged size of the focus object back to the initial size.

13. A method for relieving eye strain of a user, the method comprising the steps of:
    displaying a single focus object on a display screen; and
    providing a plurality of eye exercises using the focus object, each of the eye exercises involving at least one of the following: moving the focus object in a predetermined pattern on the display screen, and changing a size of the focus object on the display screen,
    wherein the user's eyes are exercised by viewing the focus object on the display screen, and
    wherein the plurality of eye exercises include a fourth eye exercise comprising the steps of:
    providing the focus object of an initial size at a first corner of the display screen, and moving the focus object in a diagonal direction to a third corner of the display screen while increasing the size of the focus object until the focus object reaches a predetermined enlarged size,
    providing the focus object of the initial size at a second corner of the display screen, and moving the focus object in a diagonal direction to a fourth corner of the display screen while increasing the size of the focus object until the focus object reaches the predetermined enlarged size, providing the focus object of the initial size at the third corner of the display screen, and moving the focus object in a diagonal direction to the first corner of the display screen while increasing the size of the focus object until the focus object reaches the predetermined enlarged size, and providing the focus object of the initial size at the fourth corner of the display screen, and moving the focus object in a diagonal direction to the second corner of the display screen while increasing the size of the focus object until the focus object reaches the predetermined enlarged size.

14. A method for relieving eye strain of a user, the method comprising the steps of:

displaying a single focus object on a display screen; and providing a plurality of eye exercises using the focus object, each of the eye exercises involving at least one of the following: moving the focus object in a predetermined pattern on the display screen, and changing a size of the focus object on the display screen, wherein the user's eyes are exercised by viewing the focus object on the display screen, and wherein the plurality of eye exercises include a fifth eye exercise comprising the steps of:

providing the focus object of an initial size at one corner of the display screen, moving the focus object in a diagonal direction to another corner of the display screen while increasing the size of the focus object until the focus object reaches a predetermined enlarged size, and then moving the enlarged focus object in a diagonal direction to said one corner while decreasing the size of the focus object to the initial size, and repeating said providing and moving steps at different corners of the display screen.

15. A method for relieving eye strain of a user, the method comprising the steps of:

displaying a single focus object on a display screen; and providing a plurality of eye exercises using the focus object, each of the eye exercises involving at least one of the following: moving the focus object in a predetermined pattern on the display screen, and changing a size of the focus object on the display screen, wherein the user's eyes are exercised by viewing the focus object on the display screen, and wherein the plurality of eye exercises include a sixth eye exercise comprising the steps of:

providing the focus object of an initial size at a first corner of the display screen, moving the focus object in a first direction to the center of the display screen while increasing the size of the focus object, and then moving the focus object in a second direction to a second corner of the display screen while decreasing the size of the focus object.

16. The method of claim 15, wherein the first and second directions form an angle between 0 and 180 degrees.

17. A computer program product embodied on computer readable media readable by a computing device, for relieving eye strain of a user, the product comprising computer executable instructions for:

displaying a single focus object on a display screen;

providing a plurality of eye exercises using the focus object, each of the eye exercises involving at least one of the following: moving the focus object in a predetermined pattern on the display screen, and changing the size of the focus object on the display screen, wherein the user's eyes are exercised by viewing the focus object on the display screen; and display a menu screen for receiving selections from the user, wherein the user's selections include at least one of the following: a selection of an order in which the eye exercises are executed, a selection of a particular shape and/or color of the focus object, a selection of a speed at which the focus object moves on the display screen, a selection of a background color, a selection of a particular graphical image or picture to be displayed inside the focus object, a selection of a background music or song to be played while the eye exercises are carried out, and a selection of the number of times each exercise is repeated.

18. The computer program product of claim 17, wherein the plurality of eye exercises include a first eye exercise, and the computer executable instructions for providing the first eye exercise include computer executable instructions for:

moving the focus object from a first corner of the display screen to a second corner of the display screen, moving the focus object from the second corner to a third corner of the display screen, moving the focus object from the third corner to a fourth corner of the display screen, and moving the focus object from the fourth corner to the first corner.

19. The computer program product of claim 18, wherein the computer executable instructions for moving the focus object for the first eye exercise move the focus object while maintaining the size of the focus object.

20. The computer program product of claim 18, wherein the computer executable instructions for moving the focus object for the first eye exercise move the focus object as a shape of the focus object changes.

21. The computer program product of claim 17, wherein the plurality of eye exercises include a third eye exercise, and the computer executable instructions for providing the third eye exercise include computer executable instructions for:

providing the focus object at a center of the display screen, and moving the focus object in a spiral pattern.

22. A computer program product embodied on computer readable media readable by a computing device, for relieving eye strain of a user, the product comprising computer executable instructions for:

displaying a single focus object on a display screen; and providing a plurality of eye exercises using the focus object, each of the eye exercises involving at least one of the following: moving the focus object in a predetermined pattern on the display screen, and changing the size of the focus object on the display screen, wherein the user's eyes are exercised by viewing the focus object on the display screen, and wherein the plurality of eye exercises include a fifth eye exercise, and the computer executable instructions for providing the fifth eye exercise include computer executable instructions for:

providing the focus object of an initial size at one corner of the display screen, moving the focus object in a diagonal direction to another corner of the display screen while increasing the size of the focus object until the focus object reaches a predetermined enlarged size, and then moving the enlarged focus object in a diagonal direction to said one corner while decreasing the size of the focus object to the initial size, and repeating said providing and moving steps at different corners of the display screen.

23. A computer program product embodied on computer readable media readable by a computing device, for relieving eye strain of a user, the product comprising computer executable instructions for:

displaying a single focus object on a display screen; and providing a plurality of eye exercises using the focus object, each of the eye exercises involving at least one of the following: moving the focus object in a predetermined pattern on the display screen, and changing the size of the focus object on the display screen, wherein the user's eyes are exercised by viewing the focus object on the display screen, and wherein the plurality of eye exercises include a sixth eye exercise, and the computer executable instructions for providing the sixth eye exercise include computer executable instructions for:

providing the focus object of an initial size at a first corner of the display screen, moving the focus object in a first direction to the center of the display screen while increasing the size of the focus object, and then moving the focus object in a second direction to a second corner of the display screen while decreasing the size of the focus object.

24. The computer program product of claim 23, wherein the first and second directions form an angle between 0 and 180 degrees.

25. The computer program product of claim 17, wherein the focus object is a circle, a triangle, or a rectangle.

26. The computer program product of claim 17, wherein, in the eye exercises, the user need not input a response while viewing the focus object.

27. A computer program product embodied on computer readable media readable by a computing device, for relieving eye strain of a user, the product comprising computer executable instructions for:

displaying a single focus object on a display screen; and providing a plurality of eye exercises using the focus object, each of the eye exercises involving at least one of the following: moving the focus object in a predetermined pattern on the display screen, and changing the size of the focus object on the display screen, wherein the user's eyes are exercised by viewing the focus object on the display screen, and wherein the plurality of eye exercises include a second eye exercise, and the computer executable instructions for providing the second eye exercise include computer executable instructions for:

providing the focus object of an initial size at a center of the display screen, increasing the size of the focus object until the focus object reaches a predetermined enlarged size, and then decreasing the enlarged size of the focus object back to the initial size on the display screen.

28. A computer program product embodied on computer readable media readable by a computing device, for relieving eye strain of a user, the product comprising computer executable instructions for:

displaying a single focus object on a display screen; and providing a plurality of eye exercises using the focus object, each of the eye exercises involving at least one of the following: moving the focus object in a predetermined pattern on the display screen, and changing the size of the focus object on the display screen, wherein the user's eyes are exercised by viewing the focus object on the display screen, and wherein the plurality of eye exercises include a fourth eye exercise, and the computer executable instructions for providing the fourth eye exercise include computer executable instructions for:

providing the focus object of an initial size at a first corner of the display screen, and moving the focus object in a diagonal direction to a third corner of the display screen while increasing the size of the focus object until the focus object reaches a predetermined enlarged size, providing the focus object of the initial size at a second corner of the display screen, and moving the focus object in a diagonal direction to a fourth corner of the display screen while increasing the size of the focus object until the focus object reaches the predetermined enlarged size, providing the focus object of the initial size at the third corner of the display screen, and moving the focus object in a diagonal direction to the first corner of the display screen while increasing the size of the focus object until the focus object reaches the predetermined enlarged size, and providing the focus object of the initial size at the fourth corner of the display screen, and moving the focus object in a diagonal direction to the second corner of the display screen while increasing the size of the focus object until the focus object reaches the predetermined enlarged size.

29. A computer program product embodied on computer readable media readable by a computing device, for relieving eye strain of a user, the product comprising computer executable instructions for:

displaying a single focus object on a display screen;

providing a plurality of eye exercises using the focus object, each of the eye exercises involving at least one of the following: moving the focus object in a predetermined pattern on the display screen, and changing the size of the focus object on the display screen, wherein the user's eyes are exercised by viewing the focus object on the display screen, and wherein the focus object is a circle, a triangle, or a rectangle; and displaying an image inside the focus object.

* * * * *